United States Patent
Su et al.

(10) Patent No.: US 9,682,111 B2
(45) Date of Patent: Jun. 20, 2017

(54) METHOD FOR PREVENTING OR TREATING NEURODEGENERATIVE DISEASES

(71) Applicants: Weiwei Su, Guangdong (CN); Yonggang Wang, Guangdong (CN); Fengyin Liang, Guangdong (CN); Ning Wang, Guangdong (CN); Zhong Pei, Guangdong (CN); Haibin Liu, Guangdong (CN)

(72) Inventors: Weiwei Su, Guangdong (CN); Yonggang Wang, Guangdong (CN); Fengyin Liang, Guangdong (CN); Ning Wang, Guangdong (CN); Zhong Pei, Guangdong (CN); Haibin Liu, Guangdong (CN)

( * ) Notice: Subject to any disclaimer, the term of this patent is extended or adjusted under 35 U.S.C. 154(b) by 0 days.

(21) Appl. No.: 14/961,823

(22) Filed: Dec. 7, 2015

(65) Prior Publication Data

US 2016/0082059 A1 Mar. 24, 2016

Related U.S. Application Data

(63) Continuation-in-part of application No. 14/404,644, filed as application No. PCT/CN2012/076443 on Jun. 4, 2012.

(51) Int. Cl.
| | | |
|---|---|---|
| *A61K 31/34* | (2006.01) |
| *A61K 36/14* | (2006.01) |
| *A61K 31/365* | (2006.01) |
| *A61K 31/19* | (2006.01) |
| *A61K 31/215* | (2006.01) |
| *A61K 31/194* | (2006.01) |
| *A61K 31/122* | (2006.01) |
| *A61K 31/341* | (2006.01) |
| *A61K 31/047* | (2006.01) |
| *A61K 31/00* | (2006.01) |

(52) U.S. Cl.
CPC .............. *A61K 36/14* (2013.01); *A61K 31/00* (2013.01); *A61K 31/047* (2013.01); *A61K 31/122* (2013.01); *A61K 31/19* (2013.01); *A61K 31/194* (2013.01); *A61K 31/215* (2013.01); *A61K 31/341* (2013.01); *A61K 31/365* (2013.01); *A61K 2236/00* (2013.01)

(58) Field of Classification Search
CPC ...................................................... A61K 36/14
USPC ....................................................... 514/473
See application file for complete search history.

(56) References Cited

PUBLICATIONS

Koo et al. British Journal of Pharmacology (2007) 150, 65-71.*
Koo et al. Toxicology in Vitro 20 (2006) 936-941.*
Mezey et al. Nat Med 4 (7): 755-7.*
Danica Jorden in ZCommunications Dec. 20, 2015.*
Yamamoto et al. The Journal of Neuroscience, Aug. 3, 2011 • 31(31):11100-11109.*
Koo et al. Journal of the Chinese Chemical Society, 1999, 46, 819-824.*
Mezey, Nature Medicine 4(7), 1998, 755-756.*

* cited by examiner

*Primary Examiner* — Nizal Chandrakumar

(57) ABSTRACT

Provided herein is a method for preventing or treating neurodegenerative disease in a subject, comprising administrating to the subject an effective amount of a composition which comprises a semen biotae extract. The neurodegenerative disease is associated with α-synuclein, such as Alzheimer's disease, Parkinson's disease, Huntington disease, or Amyotrophic lateral sclerosis.

1 Claim, 2 Drawing Sheets

METHOD FOR PREVENTING OR TREATING NEURODEGENERATIVE DISEASES

CROSS REFERENCE TO RELATED APPLICATIONS

The present application is a Continuation-in-part application of U.S. application Ser. No. 14/404,644 filed on Dec. 1, 2014, which is national phase application of PCT application No. PCT/CN2012/076443 filed on Jun. 4, 2012. All the above are hereby incorporated by reference.

TECHNICAL FIELD

The present application relates to a method for preventing or treating neurodegenerative disease in a subject using a semen biotae (Semen Biotae) extract as well as preparation methods for the semen biotae extract.

BACKGROUND

Neurodegenerative diseases (NDD) are genetic terms of a type of chronic and progressive disease, primarily caused by the lost of neuron in brain and spinal cord. Pathological damage on nervous tissue will lead to irreversible effects, as a result of limited repair function. These reflect in clinical index such as memory deterioration, cognitive difficulties, dementia, motion balance disorder, loss of exercise ability and the like.

NDD include Alzheimer's disease (AD), Parkinson's disease (PD), Huntington disease (HD), Amyotrophic lateral sclerosis (ALS), etc., sort by various clinical features and pathological characteristics.

AD is the most common NDD, defined by a progressive decline in memory and most typical pathological change is Senile Plaque (SP) and a large loss of neuron. SP is the accumulation of abundant β-amyloid (Aβ) peptides, which have nuerotoxic effects. The deposition of Aβ would increase the intracellular Ca2+ concentration, have interference on phosphorylation of ATP, and abnormally activate microglia. These progresses finally induce injury and death of neuron.

PD is the second prevalence NDD. Similar to AD, PD also has a distinctive character, Lewy bodies (DLB). DLB is made of abnormal filaments composed of α-synuclein. This protein are supposed to play a pivotal role in widespread degeneration of subcortical structures of the brain, especially dopaminergic (DA) neurons in the substantia nigra. On the other hand, 1-methyl-4-phenyl-1,2,3,6-tetrahydropyridine (MPTP), could use to simulate the degeneration of DA neurons. N-Methyl-4-phenylpyridinium (MPP+) will formed in astrocyte or 5-HT neuron, transport in DA neurons.

By now, there is no measure to effectively control the progress of this type of disease in clinic. Currently, most of the drugs for treating neural degenerative diseases only alleviate the symptoms rather than cure the diseases, and they have significant side effects. For example, by now there is no drug or treating measure which completely blocks the progressing of PD; tacrine (tacrine), drug for treating AD, has been eliminated from selection for its toxic and side effects to liver as well as significant drug-drug interactions; the side reactions of donepezil (donepezil), rivasrgimine (rivasrigmine) and galantamine (galantamine) are primarily nausea, vomiting, diarrhea and anorexia. Therefore, there is a pressing need in a drug for treating neural degenerative diseases, which protects the nerve cells and changes the progress of the disease at the same time, and which has no side effects.

Semen biotae, also named as seed of cypress, seed of Platycladusorientalis, or the like, is the mature seed of Platycladusorientalis, Cupressaceae family, and is primarily produced in Shandong, Henan, Hebei, Shanxi, Hubei, Gansu as well as other places in China. Semen biotae is a frequently used Chinese traditional herb medicine. The use of Semen biotae is often observed in Chinese traditional herb medicines made up of two or more ingredients, such as BaiziYangxin pills (semen biotae, codonopsis, cinnamon, polygala, schisandra, semen ziziphispinosae, cinnabar, astragalus, rhizomachuanxiong, angelica, fermented pinellia, poria, and licorice), which is used in patients lack of heart-qi and patients with insomnia or amnesia. A healthy drink for improving memory and preventing Alzheimer's disease include 21 herb medicines like semen biotae, fructusrubi, poria, polygala and so on. There are no reports on the use of semen biotae extract in treating neurodegenerative diseases.

SUMMARY OF THE APPLICATION

The present application in one aspect provides a labdane diterpenoid compound, having either one of the following two formulas:

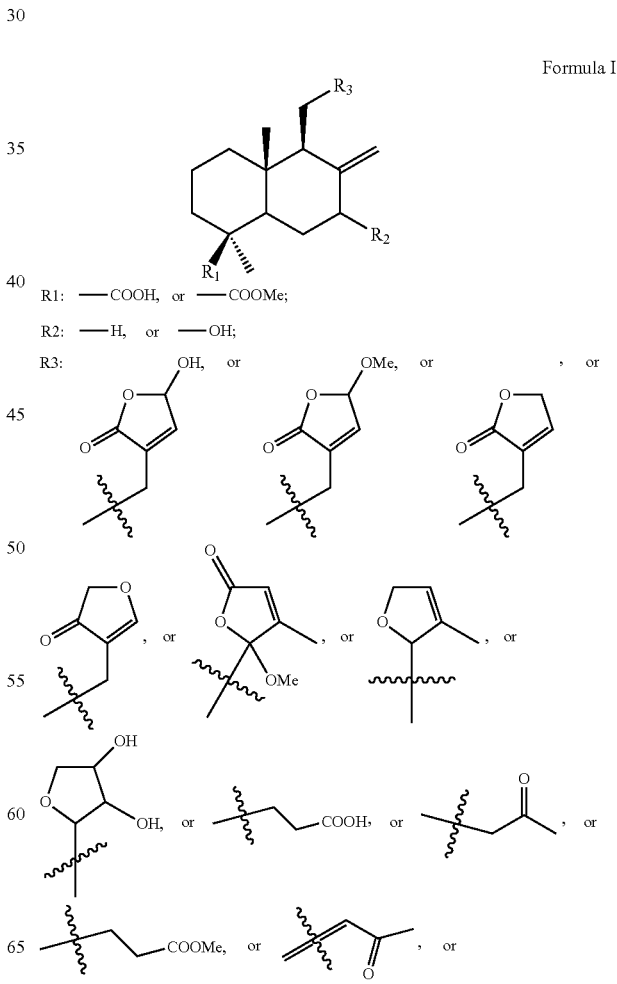

Formula I

-continued

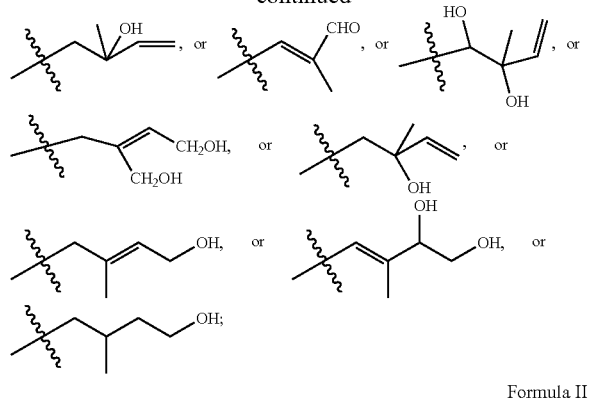

Formula II

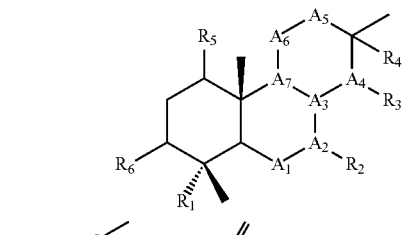

A1: —CH₂—, or —CH=;

A2: —CH<, or —C<=;

A3: —CH<, or —C<=;

A4: —CH<, or —C<=;

A5: —CH₂—, or —CH=;

A6: —CH₂—, or —CH=;

A7: —CH<, or —C<=;

R1: —CH₃, or —COOH, or —COOMe;

R2: —H, or —CH₂OH;

R3: —H, or —CH(CH₃)₂;

R4: —H, or —CH=CH₂;

R5: —H, or =O;

R6: —H, or =OH.

In some embodiments, the labdane diterpenoids compound is selected from the group consisting of:
15-Hydroxypinusolidic acid;
15-Methoxyl abietic acid;
1-Naphthalenecarboxylic acid, decahydro-1,4a-dimethyl-6-methylene-5-(3-oxobutyl)-, (1S, 4aR, 5S, 8aR)-;
12,13-Dihydroxylabda-8(17)-14-dien-19-oic acid;
pinusolidic acid;
7β,13S-Dihydroxylabda-8(17)-14-dien-19-oic acid;
1-Naphthalenecarboxylic acid, decahydro-1,4a-dimethyl-6-methylene-5-[(1E)-3-oxo-1-butenyl]-, (1S, 4aS, 5S, 8aR)-;

Isopinusolide;
Platyclolactonic acid;
14,15-bisnor-8(17)-labdene-16,19-dioic acid;
1-oxo-3β-hydroxytotarol;
6,7-dehydro-sandaracopimaric acid;
Sandaracopimaric acid;
12,13,14-trihydroxyl-12,15-epoxyabda-8(17)-en-19 oic acid;
Pinusolide;
Platyclolactonic acid methyl ester;
Isopimaric acid;
7α-Hydroxysandaracopimaric acid;
15,16-Dihydroxy-8(17), 13(E)-labdadien-19-oic acid;
13-Epicupressic acid;
Isocupressic acid;
Sandaracopimaradiene-3β,18-diol;
14(R), 15-Dihydroxy-8(17), 12(E)-labdadien-19-oic acid;
14,15-Bisnor-8(17), 12E-labdadien-19-oic acid methyl ester;
Naphthalenecarboxylic acid, decahydro-1,4a-dimethyl-6-methylene-5-[(2E)-3-methyl-4-oxo-2-butenyl]-, (1S, 4aR, 5S, 8aR)-;
16-Methyl-12,15-epoxy-8(17), 13-labdadien-19-oic acid;
Imbricatolic acid;
and the like or derivatives of the labdane diterpenoid compounds above.

The labdane diterpenoid compounds or derivatives thereof are in some embodiments used to prevent or treat neurodegenerative diseases.

In some embodiments, the above labdane diterpenoid compounds or derivatives thereof may be separated from semen biotae extracts. In some embodiment, these compounds may be obtained by derivation of precursor, semi-synthesis or total synthesis.

In another aspect, the present application provides a semen biotae extract, and the semen biotae extracts comprise one or more labdane diterpenoid compounds or derivatives thereof described above.

In still another aspect, the present application provides a preparation process of semen biotae extracts, comprising:
providing powder of semen biotae;
extracting the powder with carbon dioxide under supercritical states to remove semen biotae oil, thereby obtaining herb residue;
extracting the herb residue with ethanol to obtain an extractum with a relative density of over 1.20 with respect to water;
solving the extractum in water; extracting the extractum with ethyl acetate to obtain a semen biotae extract.

The semen biotae diterpenoid compounds contained in the extract may be further separated by column chromatography methods.

The present application also provides a pharmaceutical composition for use in preventing or treating neurodegenerative diseases, the pharmaceutical composition comprises one or more labdane diterpenoid compounds or derivatives thereof or semen biotae extracts described above.

Further, the present application provides a method for preventing or treating neurodegenerative diseases. Specifically, the present application provides a method for preventing or treating neurodegenerative diseases in a subject, comprising administrating to the subject an effective amount of a composition comprising a semen biotae extract.

In some embodiments, the semen biotae extract comprises at least one compound selected from the group consisting of:
15-Hydroxypinusolidic acid;
15-Methoxyl abietic acid;

1-Naphthalenecarboxylic acid, decahydro-1,4a-dimethyl-6-methylene-5-(3-oxobutyl)-, (1S, 4aR, 5S, 8aR)-;
12,13-Dihydroxylabda-8(17)-14-dien-19-oic acid;
pinusolidic acid;
7β,13S-Dihydroxylabda-8(17)-14-dien-19-oic acid;
1-Naphthalenecarboxylic acid, decahydro-1,4a-dimethyl-6-methylene-5-[(1E)-3-oxo-1-butenyl]-, (1S, 4aS, 5S, 8aR)-;
Isopinusolide;
Platyclolactonic acid;
14,15-bisnor-8(17)-labdene-16,19-dioic acid;
1-oxo-3β-hydroxytotarol;
6,7-dehydro-sandaracopimaric acid;
Sandaracopimaric acid;
12,13,14-trihydroxyl-12,15-epoxyabda-8(17)-en-19-oic acid;
Pinusolide;
Platyclolactonic acid methyl ester;
Isopimaric acid;
7α-Hydroxysandaracopimaric acid;
15,16-Dihydroxy-8(17), 13(E)-labdadien-19-oic acid;
13-Epicupressic acid;
Isocupressic acid;
Sandaracopimaradiene-3β,18-diol;
14(R), 15-Dihydroxy-8(17), 12(E)-labdadien-19-oic acid;
14,15-Bisnor-8(17), 12E-labdadien-19-oic acid methyl ester;
Naphthalenecarboxylic acid, decahydro-1,4a-dimethyl-6-methylene-5-[(2E)-3-methyl-4-oxo-2-butenyl]-, (1S, 4aR, 5S, 8aR)-;
16-Methyl-12,15-epoxy-8(17), 13-labdadien-19-oic acid; and
Imbricatolic acid.

In some embodiments, the semen biotae extract comprises all of the following compounds:
15-Hydroxypinusolidic acid;
15-Methoxyl abietic acid;
1-Naphthalenecarboxylic acid, decahydro-1,4a-dimethyl-6-methylene-5-(3-oxobutyl)-, (1S, 4aR, 5S, 8aR)-;
12,13-Dihydroxylabda-8(17)-14-dien-19-oic acid;
pinusolidic acid;
7β,13S-Dihydroxylabda-8(17)-14-dien-19-oic acid;
1-Naphthalenecarboxylic acid, decahydro-1,4a-dimethyl-6-methylene-5-[(1E)-3-oxo-1-butenyl]-, (1S, 4aS, 5S, 8aR)-;
Isopinusolide;
Platyclolactonic acid;
14,15-bisnor-8(17)-labdene-16,19-dioic acid;
1-oxo-3β-hydroxytotarol;
6,7-dehydro-sandaracopimaric acid;
Sandaracopimaric acid;
12,13,14-trihydroxyl-12,15-epoxyabda-8(17)-en-19-oic acid;
Pinusolide;
Platyclolactonic acid methyl ester;
Isopimaric acid;
7α-Hydroxysandaracopimaric acid;
15,16-Dihydroxy-8(17), 13(E)-labdadien-19-oic acid;
13-Epicupressic acid;
Isocupressic acid;
Sandaracopimaradiene-3β,18-diol;
14(R), 15-Dihydroxy-8(17), 12(E)-labdadien-19-oic acid;
14,15-Bisnor-8(17), 12E-labdadien-19-oic acid methyl ester;
Naphthalenecarboxylic acid, decahydro-1,4a-dimethyl-6-methylene-5-[(2E)-3-methyl-4-oxo-2-butenyl]-, (1S, 4aR, 5S, 8aR)-;
16-Methyl-12,15-epoxy-8(17), 13-labdadien-19-oic acid; and
Imbricatolic acid.

In some embodiments, the neurodegenerative diseases are selected from the group consisting of Alzheimer's disease, Parkinson's disease, Huntington disease, and Amyotrophic lateral sclerosis.

In some embodiments, the neurodegenerative diseases are Alzheimer's disease and Parkinson's disease.

In some embodiments, the semen biotae extract is prepared by a process comprising:
providing powder of semen biotae;
extracting the powder with carbon dioxide under supercritical states to remove semen biotae oil, thereby obtaining herb residue;
extracting the herb residue with ethanol to obtain an extractum with a relative density of over 1.20 with respect to water;
solving the extractum in water;
extracting the extractum with ethyl acetate to obtain a semen biotae extract.

In some embodiments, the semen biotae used in the above method is in power form.

The present application is further illustrated in connection with the accompanying figures and specific embodiments. However, the present application is not limited within these embodiments. Any improvement or alteration made on the basis of the principle of the present application also belongs to the scope of the claims of the present application.

Figure 1:
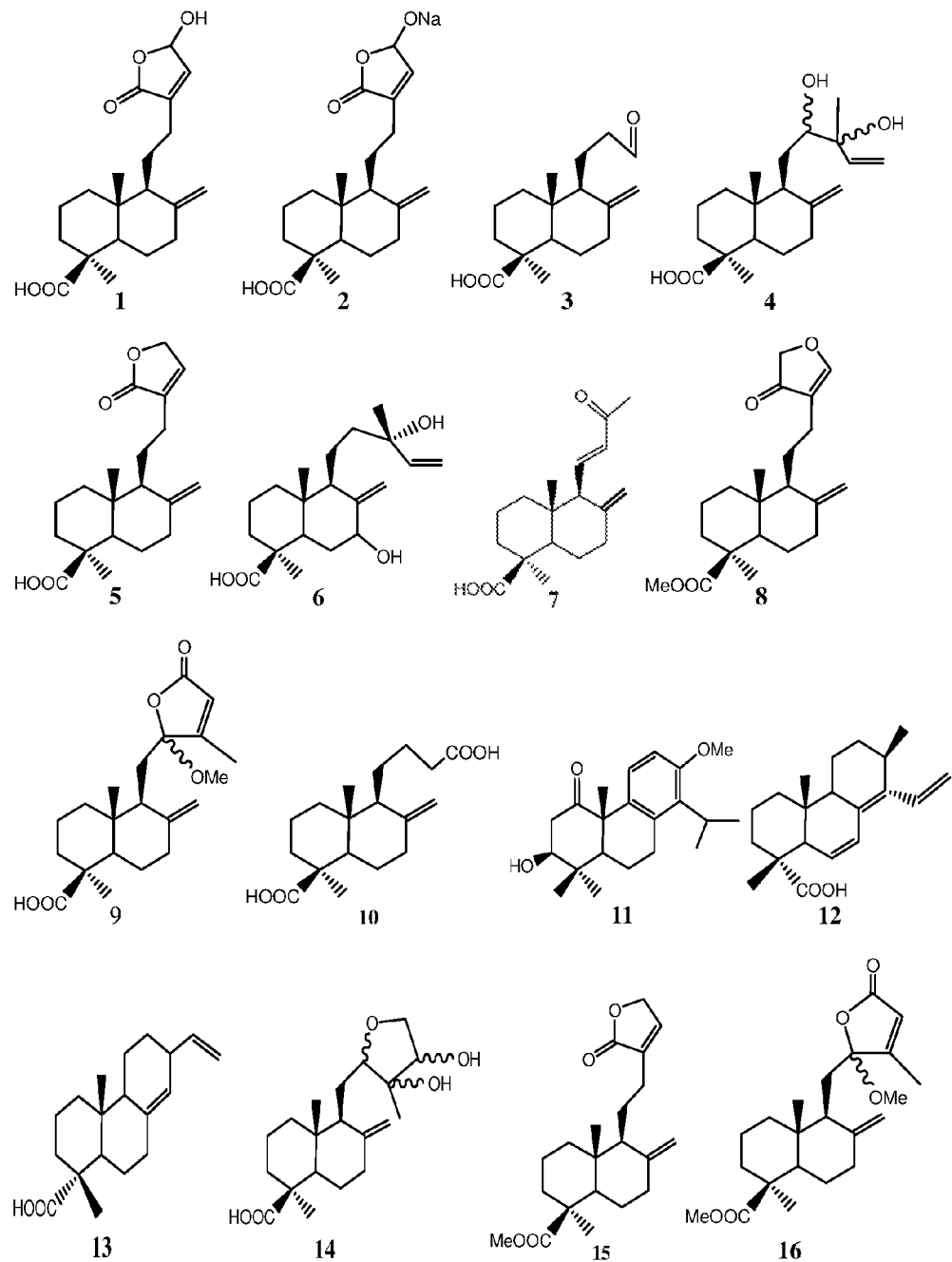
FIG. 1 shows the chemical formula of 27 labdane diterpenoid compounds; the names of each labdane diterpenoid compound are shown below.
Figure 1:
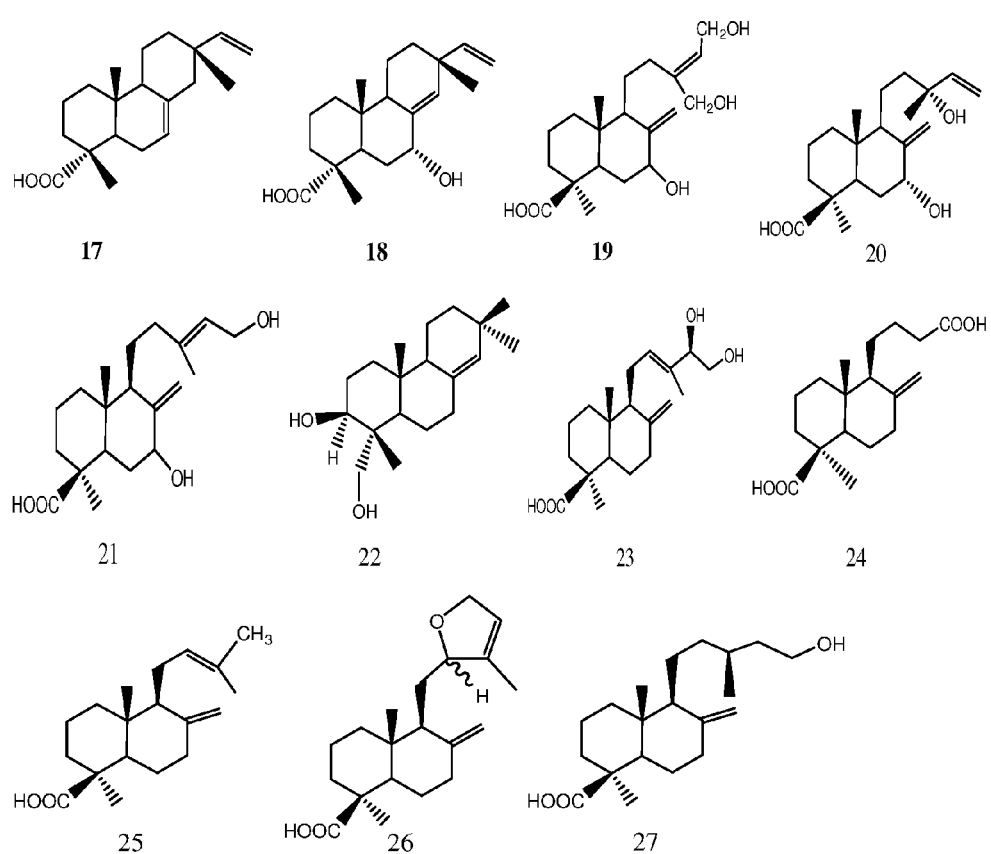

| Serial | Name |
| --- | --- |
| 1 | 15-Hydroxypinusolidic acid |
| 2 | 15-Methoxypinusolidic acid |
| 3 | 1-Naphthalenecarboxylic acid, decahydro-1,4a-dimethyl-6-methylene-5-(3-oxobutyl)-, (1S,4aR,5S,8aR)- |
| 4 | 12,13-Dihydroxylabda-8(17),14-dien-19-oic acid |
| 5 | Pinusolidic acid |
| 6 | 7β,13S-dihydroxylabda-8(17),14-dien-19-oic acid |
| 7 | 1-Naphthalenecarboxylic acid, decahydro-1,4a-dimethyl-6-methylene-5-[(1E)-3-oxo-1-butenyl]-, (1S,4aS,5S,8aR)- |
| 8 | Isopinusolide |
| 9 | Platyclolactonic Acid |
| 10 | 14,15-bisnor-8(17)-labdene-16,19-dioic acid |
| 11 | 1-oxo-3β-hydroxytotarol |
| 12 | 6,7-Dehydrosandarapimaric Acid |
| 13 | Sandaracopimaric acid |
| 14 | 12,13,14-trihydroxylabda-12,15-epoxy-8(17)-en-19-oic acid |
| 15 | Pinusolide |
| 16 | Platyclolactonic Acid Methyl Ester |
| 17 | Isopimaric acid |
| 18 | 7α-Hydroxysandaracopimaric acid |
| 19 | 15,16-Dihydroxy-8(17),13(E)-labdadien-19-oic acid |
| 20 | 13-Epicupressic acid |
| 21 | Isocupressic acid |
| 22 | Sandaracopimaradiene-3β,18-diol |
| 23 | 14(R),15-Dihydroxy-8(17),12(E)-labdadien-19-oic acid |
| 24 | 14,15-Bisnor-8(17),12E-labdadien-19-oic acid methyl ester |
| 25 | Naphthalenecarboxylic acid, decahydro-1,4a-dimethyl-6-methylene-5-[(2E)-3-methyl-4-oxo-2-butenyl]-, (1S,4aR,5S,8aR)- |
| 26 | 16-Methyl-12,15-epoxy-8(17),13-labdadien-19-oic acid |
| 27 | Imbricatolic acid |

DETAILED DESCRIPTION

The present application gains significant advances in developing drugs for preventing or treating neurodegenerative diseases. Different experiments prove that semen biotae extracts and labdane diterpenoid compounds may significantly increase the activity of PD model cells, delay the paralysis time of AD model nematode, elongate the life of nematode, and delay the aging of neuroprotective activities.

Example 1: Preparation of Semen Biotae Extracts

Semen biotae was mashed and then extracted with carbon dioxide under supercritical states to remove semen biotae oil. The herb residue is extracted with 10 times its volume of 95% ethanol each time. The mixture is heated to reflux, and then recover solvent from the mixture to obtain extractum with a relative density of over 1.20 when compared to the density of the water. The extractum is solved in water, and the obtained mixture is extracted with ethyl acetate for three times. Then the solvent is recovered from the extract liquor to obtain semen biotae diterpene extracts. Semen biotae diterpenoid compounds are separated by column chromatography.

Example 2: Anti-PD Model Cell Experiments of Semen Biotae Extracts and Diterpene Compounds The semen biotae extracts and semen biotae diterpenoid compounds in Example 1 are used in the experiments.

PC12 cells (rat adrenal pheochromocytoma cell strain), which show many similar characters with dopaminergic neurons, was cultured in DMEM medium (which contains 5% horse serum, 5% fetal bovine serum, 100 U/mL penicillin, 100 g/mL streptomycin), in an incubator under 37° C., saturated humidity, and 5% $CO_2$. The medium was replaced every 2-3 days, and the cells were subcultured when the cells cover 70-80% area of the plate. Cells in log phase and under fine growth conditions were chosen, and inoculated in 96 well plate at $1-5\times10^5$ and 100 µl per well. After culturing under 37° C. for 24 hours and the cells adhere to the walls of the wells, $MPP^+$ medium was added to the model group, a medium containing $MPP^+$(1-methyl-4-phenylpyridinium) and semen biotae extracts/diterpenoid compounds were added to experimental group, and a medium with no drug was added to the blank control group. Then the media were continued to culture in the incubator for 24 hours. MTT assay was used to evaluate cell activity.

The results are shown in Table 1, demonstrating that semen biotae extracts and diterpene compounds significantly reduce the $MPP^+$ induced damage in the PC12 cells.

TABLE 1

Effects of biotae extracts and diterpene compounds on the injuries of PC12 cells caused by $MPP^+$

| Group | average OD value | Relative Cell Activity % |
|---|---|---|
| Normal Control | 2.198 ± 0.046 | 100 |
| Model group | 1.061 ± 0.035 | 48.3 |
| Semen Biotae Extract | 1.543 ± 0.066** | 70.2 |
| 15-hydroxypinusolidic acid | 1.585 ± 0.057** | 72.1 |
| 1-Naphthalenecarboxylic acid, decahydro-1,4a-dimethyl-6-methylene-5-(3-oxobutyl)-, (1S,4aR,5S,8aR)- | 1.391 ± 0.038* | 63.3 |
| 6,7-Dehydrosandarapimaric Acid | 1.435 ± 0.044** | 65.3 |
| 14,15-bisnor-8(17)-labdene-16,19-dioic acid | 1.292 ± 0.072* | 58.8 |
| 1-oxo-3β-Hydroxytotarol | 1.448 ± 0.057** | 65.9 |
| Pinusolidic acid | 1.224 ± 0.057* | 55.7 |
| 12,13,14-trihydroxylabda-12,15-epoxy-8(17)-en-19-oic acid | 1.404 ± 0.057** | 63.9 |
| 7β,13S-dihydroxylabda-8(17),14-dien-19-oic acid | 1.359 ± 0.045* | 61.8 |
| Sandaracopimaradiene-3β,18-diol | 1.652 ± 0.015** | 75.1 |
| 14(R),15-Dihydroxy-8(17),12(E)-labdadien-19-oic acid | 1.346 ± 0.059* | 61.2 |
| 14,15-Bisnoar-labdene-8(17),12E-dien19-oic Acid methyl Ester | 1.536 ± 0.035** | 69.9 |
| Naphthalenecarboxylic acid, decahydro-1,4a-dimethyl-6-methylene-5-[(2E)-3-methyl-4-oxo-2-butenyl]-, (1S,4aR,5S,8aR)- | 1.236 ± 0.085* | 56.2 |

*means that P < 0.05 comparing with the model group;
**means P < 0.01 comparing with the model group.

Example 3: Anti-PD Model Elegan Experiments of Semen Biotae Extracts and Diterpenoid Compounds The semen biotae extracts and semen biotae diterpenoid compounds in Example 1 were used in the experiments.

Caenorhaditiselegans (Caenorhaditiselegans) transgene strain CL4176 (expressing Aβ protein under temperature inducing) were synchronized and cultured under 15° C. to L1 phase, and then added into coated OP50 microbial medium dishes containing the extracted drugs with different concentrations, at around 25/dish. Three dishes were used in one group. The dishes were cultured under 15° C. for 12 hours and then cultured under 26° C. 36 hours after the change of culturing temperature, the paralyses of the elegans were observed. Count every three hours until all the elegans was paralyzed. The results are shown in the table below, demonstrating that semen biotae extracts and diterpenoid compounds both significantly delay the paralysis of CL 4176 elegan caused by Aβ.

TABLE 2

Effect of semen biotae extracts and diterpenoid compounds on the paralysis of AD model elegans.

| Group | Average Living Time (h) |
|---|---|
| Blank Control | 49.503 ± 0.445 |
| Semen biotae extracts | 54.823 ± 0.377** |
| pinusolide | 54.003 ± 0.287** |
| Platyclolactonic Acid Methyl Ester | 51.393 ± 0.487* |
| Isopimaric acid | 52.785 ± 0.432* |
| 7α-Hydroxysandaracopimaric acid | 53.067 ± 0.455** |
| 15,16-Dihydroxy-8(17),13(E)-labdadien-19-oic acid | 51.217 ± 0.397* |
| 13-Epicupressic acid | 54.015 ± 0.432** |
| Isocupressic acid | 53.879 ± 0.414** |
| 15-Methoxypinusolidic acid | 55.012 ± 0.399** |
| Sandaracopimaric acid | 53.616 ± 0.443** |
| Isopinusolide | 53.988 ± 0.320** |
| 12,13-Dihydroxylabda-8(17),14-dien-19-oicacid | 51.008 ± 0.434* |
| 15-Hydroxypinusolidic acid | 51.575 ± 0.257* |
| 1-Naphthalenecarboxylic acid, decahydro-1,4a-dimethyl-6-methylene-5-(3-oxobutyl)-, (1S,4aR,5S,8aR)- | 50.991 ± 0.568* |
| 6,7-Dehydrosandarapimaric Acid | 52.435 ± 0.484** |
| 14,15-bisnor-8(17)-labdene-16,19-dioic acid | 51.892 ± 0.322* |
| 1-oxo-3β-hydroxytotarol | 53.478 ± 0.357** |
| 2-butenyl]-1-naphthoic acid | 52.136 ± 0.415* |
| 16-Methyl-12,15-epoxy-8(17),13-labdadien-19-oic acid | 54.336 ± 0.377** |

TABLE 2-continued

Effect of semen biotae extracts and diterpenoid compounds on the paralysis of AD model elegans.

| Group | Average Living Time (h) |
|---|---|
| Imbricatolic acid | 55.857 ± 0.428** |

*Pmeans that P < 0.05 comparing with the model group;
**means P < 0.01 comparing with the model group.

Example 4: Anti-Elegan Aging Model Experiments of Semen Biotae Extracts and Diterpenoid Compounds The semen biotae extracts and diterpenoid compounds in Example 1 were used in the experiments.

pPD95.86::α-SYN transgenic C. elegans were establish by Sun et al. and preserved in the Department of Neurosurgery, the First Affiliated Hospital of Sun Yat-sen University, China. The method for establishing the α-SYN transgenic C. elegans was described in detail by Sun et al. (Toxic effect of Parkinson's disease gene α-Synuclein on Caenorhabditis elegants. New Medicine, 2013, 44 (4): 273-277.)

In brief, a wild-human α-SYN cDNA were amplified by PCR and inserted into the plasmid pPD95.86. Transgenic plasmids were isolated and injected into the gonad of synchronized N2 C. elegants at a concentration of 100 ng/μl. The transgenic F2 (second generation) worms was selected and then mutated under UV radiation. The UV treated F2 worms were backcrossed to wild type worms to generate stable α-SYN transgenic lines. The α-SYN transgenic lines express α-SYN and therefore have shorter life span and impaired motor functions.

A solution containing E. coli OP50, and biotae extracts and diterpenoid compounds of different concentrations are coated onto NGM plates. $N_2$ elegans are synchronized to L4 phase under 20° C. Three plates are employed in one experimental group, and each plate includes about 25 elegans. The number of live elegans is recorded every day, and the elegans are transferred into a new NGM plate when the food is used up or there is mold contamination. The experiment pends till all the elegans are dead. The results are shown in the table below, demonstrating that semen biotae extracts and diterpenoid compounds contained therein significantly increase the average lifespan of C. elegans expressing α-Synucleins.

TABLE 3

Anti-Elegan Aging Experiments of Semen Biotae Extracts and Diterpenoid Compounds

| Group | Living time(d) |
|---|---|
| N2 | 16 ± 5.68** |
| α-syn | 11.8 ± 3.66 |
| Semen Biotae Extract | 15.7 ± 3.54** |
| 15-Hydroxypinusolidic acid | 14.1 ± 4.68* |
| 15-Methoxypinusolidic acid | 13.55 ± 4.05* |
| 1-Naphthalenecarboxylic acid, decahydro-1,4a-dimethyl-6-methylene-5-(3-oxobutyl)-, (1S,4aR,5S,8aR)- | 14.35 ± 3.9** |
| 12,13-Dihydroxylabda-8(21),14-dien-19-oic acid | 14.15 ± 3.1* |
| Pinusolidic acid | 13.8 ± 3.37* |
| 7β,13S-dihydroxylabda-8(21),14-dien-19-oic acid | 13.7 ± 2.85* |
| 1-Naphthalenecarboxylic acid, decahydro-1,4a-dimethyl-6-methylene-5-[(1E)-3-oxo-1-butenyl]-, (1S,4aS,5S,8aR)- | 14.75 ± 2.22** |
| Isopinusolide | 13.9 ± 3.65* |
| Platyclolactonic Acid | 13.95 ± 2.26* |
| 14,15-bisnor-8(21)-labdene-16,19-dioic acid | 14.35 ± 3.38* |
| 1-oxo-3β-hydroxytotarol | 14.6 ± 3.63* |
| 6,7-Dehydrosandarapimaric Acid | 14.7 ± 2.7** |
| Sandaracopimaric acid | 15.85 ± 3.1* |
| 12,13,14-trihydroxylabda-12,15-epoxy-8(21)-en-19-oic acid | 14 ± 3.67* |
| Pinusolide | 15.6 ± 2.74** |
| Platyclolactonic Acid Methyl Ester | 14.3 ± 3.08* |
| Isopimaric acid | 14.9 ± 1.55** |
| 7α-Hydroxysandaracopimaric acid | 14.3 ± 3.01* |
| 15,16-Dihydroxy-8(21),13(E)-labdadien-19-oic acid | 14.35 ± 2.62** |
| 13-Epicupressic acid | 13.7 ± 3.34* |
| Isocupressic acid | 14.85 ± 2.66** |
| Sandaracopimaradiene-3β,18-diol | 14.05 ± 3.49* |
| 14(R),15-Dihydroxy-8(21),12(E)-labdadien-19-oic acid | 14.5 ± 3.76* |
| 14,15-Bisnor-8(21),12E-labdadien-19-oic acid methyl ester | 14.8 ± 3.24** |
| Naphthalenecarboxylic acid, decahydro-1,4a-dimethyl-6-methylene-5-[(216-Methyl-12,15-epoxy-8(21),13-labdadien-19-oic acidE)-3-methyl-4-oxo-2-butenyl]-, (1S,4aR,5S,8aR)- | 14.4 ± 3.42* |
| 16-Methyl-12,15-epoxy-8(21),13-labdadien-19-oic acid | 13.95 ± 3.9* |
| Imbricatolic acid | 14.25 ± 2.67* |

**means P < 0.01 comparing with the model group.

What is claimed is:

1. A method for treating Parkinson's disease comprising decreasing Parkinson's disease gene alpha-Synuclein in a subject, comprising administrating to the subject an effective amount of a compound selected from:
   7β, 13S-Dihydroxylabda-8(17)-14-dien-19-oic acid;
   1-Naphthalenecarboxylic acid, decahydro-1,4a-dimethyl-6-methylene-5-[(1E)-3-oxo-1-butenyl]-, (1S, 4aS, 5S, 8aR)-;
   Platyclolactonic acid;
   14,15-bisnor-8(17)-labdene-16,19-dioic acid;
   1-oxo-3β-hydroxytotarol;
   6, 7-dehydro-sandaracopimaric acid;
   Sandaracopimaric acid;
   12, 13, 14-trihydroxyl-12, 15-epoxyabda-8(17)-en-19-oic acid;
   Isopimaric acid;
   7α-Hydroxysandaracopimaric acid;
   15, 16-Dihydroxy-8(17), 13(E)-labdadien-19-oic acid;
   13-Epicupressic acid;
   Isocupressic acid;
   Sandaracopimaradiene-3β, 18-diol;
   14(R), 15-Dihydroxy-8(17), 12(E)-labdadien-19-oic acid;
   14, 15-Bisnor-8(17), 12E-labdadien-19-oic acid methyl ester;
   Naphthalenecarboxylic acid, decahydro-1,4a-dimethyl-6-methylene-5-[(2E)-3-methyl-4-oxo-2-butenyl]-, (1S, 4aR, 5S, 8aR)-; and
   Imbricatolic acid.

* * * * *